US006248790B1

(12) United States Patent
Uckun et al.

(10) Patent No.: US 6,248,790 B1
(45) Date of Patent: Jun. 19, 2001

(54) TREATMENT OF INFLAMMATION WITH 2,4,6-TRIHYDROXY-ALPHA-RHO-METHOXYPHENYLACETOPHENONE, OR ITS PHARMACEUTICALLY ACCEPTABLE DERIVATIVES

(75) Inventors: Fatih M. Uckun, White Bear Lake; Ravi Malaviya, St. Paul, both of MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 09/606,926

(22) Filed: Jun. 29, 2000

(51) Int. Cl.[7] .................................................. A61K 31/12
(52) U.S. Cl. ................................................................ 514/685
(58) Field of Search ............................................. 514/685

(56) References Cited

U.S. PATENT DOCUMENTS 3,879,414   4/1975   Haugwitz et al. ................ 260/309.2

FOREIGN PATENT DOCUMENTS

WO 98/08503   3/1998   (WO) .

OTHER PUBLICATIONS

Caplus Abstract, AN2000:113,592, Balasubramanian, et al., Synth. Commun. 30(3),469–484, 2000.

Chanmugam, P. et al., "Radicicol, a Protein Tryosine Kinase Inhibitor, Suppresses the Expression of Mitogen–inducible Cyclooxygenase in Macrophages Simultated with Lipopolysaccharide and in Experimental Glomerulonephritis",*The Journal of Biological Chemistry*, vol. 270 No. 10, pp. 5418–5426 (Mar. 10, 1995).

Cronstein, B. et al., "The Antiinflammatory Effects of an Adenosine Kinase Inhibitor are Medaited by Adenosine", *Arthritis & Rheumatism*, vol. 38, No.8, pp. 1040–1045 (Aug. 1995).

Dawson, J. et al., "A comparitive Study of the Cellular, Exudative and Histological Responses to Carrageenan, Dextran and Zymosan in the Mouse",*Int. J. Tiss. Reac.,* vol. XIII, No. 4, pp. 171–185 (1991).

Galli, S., "New Concepts About the Mast Cell" *The New England Journal of Medicine*, vol. 328, No. 4. pp. 257–265 (Jan. 28, 1993).

Hamawy, M. et al., "Protein Tyrosine Phosphorylation as a Mechanism of Signalling in Mast Cells and Basophils", *Cellular Signalling*, vol. 7 No. 6, pp. 535–544 (Aug. 1995).

Hruza, L. et al., "Mechanisms of UV–Induced Inflammation",*The Journal of Investigative Dermatology*, vol. 100, No. 6, pp. 35S–41S (Jun. 1993).

Humes, J. et al., "Evidence of Two Sources of Arachindonic Acid for Oxidative Metabolism by Mouse Peritoneal Macrophages", *The Journal of Biological Chemistry*, vol. 257, No. 4, pp. 1591–1594 (Feb. 25, 1982).

Konger, R. et al., "Growth regulation of primary human keratinocytes by prostaglandin E receptor $EP_2$ and $EP_3$ subtypes ", *Biochimica et Biophysica Acta*, vol. 1401, pp. 221–234 (1998).

Lepley, R. et al., "Tyrosine Kinase Activity Modulates Catalysis and Translocation of Cellular 5–Lipoxygenase", *The Journal of Biological Chemistry*, vol. 271, No. 11, pp. 6179–6184 (Mar. 15, 1995).

Levitzki, A. et al., "Tyrosine Kinase Inhibition: An Approach to Drug Development",*Science*, vol. 267, pp. 1782–1788 (Mar. 24, 1995).

Liu, F. et al., "Monoclonal Dinitrophenyl–Specific Murine IgE Antibody: Preparation, Isolation, and Characterization", *The Journal of Immunology*, vol. 124, No. 6, pp. 2728–2737 (Jun. 1980).

Mahajan, S. et al., "Rational Design and Synthesis of a Novel Anti–leukemic Agent Targeting Bruton's Tyrosine Kinase (BTK), LFM A13 [α–Cyano–β–Hydroxy–β–Methyl–N–(2,5–Dibormophenyl)Propenamide]"*The Journal of Biological Chemistry*, vol. 274, No. 14, pp. 9587–9599 (Apr. 2, 1999).

Malaviya, R. et al., "Histamine in Human Epidermal Cells is Induced by Ultraviolet Light Injury "*The Journal of Investigative Dermatology* , vol. 106, No. 4, pp. 785–789 (Apr. 1996).

Malaviya, R., et al., "Reversible Translocation of 5–Lipoxygenase in Mast Cells upon IgE/Antigen Stimulation", *The Journal of Biological Chemistry*, vol. 268, no. 7, pp. 4939–4944 (Mar. 5, 1993).

Malaviya, R. et al., "[3] Interaction of Bacteria with Mast Cells", *Methods in Enzymology*, vol. 253, pp. 27–43 (1995).

Malaviya, R. et al., "Clinical Implications of mast cell–bacteria interaction" , *The Journal of Molecular Medicine*, vol. 76, No. 9, pp. 617–623 (Aug. 1998).

Oettgen, H. et al., "Active anaphylaxis in IgE–deficient mice", *Nature*, vol. 370 No. 6488, pp. 367–370 (Aug. 1994).

(List continued on next page.)

*Primary Examiner*—Raymond Henley, III
(74) *Attorney, Agent, or Firm*—Mechant & Gould P.C.

(57) ABSTRACT

2,4,6-trihydroxy-α-p-methoxyphenylacetophenone (also identified herein as "D-58"), or its pharmaceutically acceptable derivatives such as salt and ester forms, is administered for inhibiting inflammatory reactions. The treatment can be remedial or prophylactic. Examples of the conditions that can be treated include acute inflammatory reactions and allergic inflammatory reactions, and specific examples include allergy, asthma, arthritis, psoriasis, skin sunburn, inflammatory pelvic disease, inflammatory bowel disease, urethritis, uvitis, senusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitis and cholangitis. The 2,4,6-trihydroxy-α-p-methoxyphenylacetophenone can be administered by various routes as needed.

23 Claims, 10 Drawing Sheets

OTHER PUBLICATIONS

Oliver, J. et al., "Inhibiton of Mast Cell FcεR1–mediated Signaling and Effector Function by the Syk–selective Inhibitor, Piceatannol",*The Journal of Biological Chemistry*, vol. 269, No. 47, pp. 29697–29703 (Nov. 25, 1994).

Ozawa, K. et al., "$Ca^{2+}$–dependent and $Ca^{2+}$–independent Isozymes of Protein Kinase C Mediate Exocytosis in Antigen–stimulated Rat Basophilic RBL–2H3 Cells", *The Journal of Biological Chemistry*, vol. 268, No. 3, pp. 1749–1756 (Jan. 25, 1993).

Perretti, M. et al., "A role for endogenous histamine in interleukin–8–induced neutrophil infiltration into mouse air– pouch: investigation of the modulatory action of systemic and local dexamethasone", *British Journal of Pharmacology*, vol. 112, No. 3, pp. 801–808 (Jul. 1994).

Sagi–Eisenberg, R., et al., "Signal–Transmission Pathways in Mast Cell Exocytosis", *Immunopharmacology of Mast Cells and Basophils*, Ch. 6, pp. 71–88 (1993).

Scharenberg, A. et al, "Early Events in Mast Cell Signal Transduction",*Human Basophils and Mast Cells: Biological Aspects. Chem Immunol.*, vol. 61, pp. 72–87 (1995).

Smith, P. et al., "Measurement of Protein Using Bicinchoninic Acid", *Analytical Biochemistry* vol. 150, No. 1, pp. 76–85 (Oct. 1985).

Smith, W., "Prostanoid biosynthesis and mechanisms of action", *American Journal of Physiology: Renal, Fluid and Electrolyte Physiology*, vol. 32, No. 2, pp. F181–F191 (Aug. 1992).

Snyder, D. et al., "Topical indomethacin and sunburn", *British Journal of Dermatology*, vol. 90, No. 1, pp. 91–93 (Jan. 1974).

Sudbeck, E. et al., "Structure–based Design of Specific Inhibitors of Janus Kinase 3 as Apoptosis–inducing Anti-leukemic Agents", *Clinical Cancer Research*, vol. 5, No. 6, pp. 1569–1582 (Jun. 1999).

Thastrup, O. et al., "Thapsigargin, a tumor promoter, discharges intracellular $Ca^{2+}$ stores by specific inhibition of the endoplasmic reticulum $Ca^{2+}$–ATPase", *Proc. Natl. Acad. Sci USA*, vol. 87, No. 7, pp. 2466–2470 (Apr. 1990).

Trieu, V. et al., "*In vivo* Antioxidant Activity of Genistein in a Murine Model of Singlet Oxygen–Induced Cerebral Stroke", *Radiation Research*, vol. 152, No. 5, pp. 508–516 (Nov. 1999).

Uckun, F. et al., "Biotherapy of B–Cell Precursor Leukemia by Targeting Genistein to CD19–Associated Tyrosine Kinases", *Science*, vol. 267, No. 5199, pp. 886–891 (Feb. 10, 1995).

Uckun, F. et al., "BTK as a Mediator of Radiation–Induced Apoptosis in DT–40 Lymphoma B Cells", *Science*, vol. 273, pp. 1096–1100. (Aug. 23, 1996).

Vassilev, A. et al., "Bruton's Tyrosine Kinase as an Inhibitor of the Fas/CD95 Death Inducing Signaling Complex", *The Journal of Biological Chemistry*, vol. 274, No. 3, pp. 1646–1656 (Jan. 15, 1999).

Wei, Y. et al., "Contribution of Macrophages to Immediate Hypersensitivity Reaction", *The Journal of Immunology*, vol. 137, No. 6, pp. 1993–2000 (Sep. 15, 1986).

Woodward, D.F. et al., "Re–evaluation of the effect of non–steroidal anti–inflammatory agents on u.v.–induced cutaneous inflammation", *Agents and Actions*, vol. 11, Nos. 6/7, pp. 711–717 (Dec. 1981).

Zhu, D. et al., "Calphostin C Triggers Calcium–dependent Apoptosis in Human Acute Lymphoblastic Leukemia Cells", *Clinical Cancer Research*, vol. 4 No. 12, pp. 2967–2976 (Dec. 1998).

C. Lack of HCK Inhibition (IC$_{50}$ > 200 μM)

Compound D-58 (μM)

BTK (IC$_{50}$ = 35.3 μM)

| | CON | 10 | 50 | 75 | 100 | 200 |
|---|---|---|---|---|---|---|
| PIU | 3708 | 4107 | 1290 | 560 | 323 | 21 |
| % Con | 100 | 111 | 34.8 | 15.1 | 8.7 | 0.6 |

SYK (IC$_{50}$ < 10 μM)

| | CON | 10 | 50 | 75 | 100 | 200 |
|---|---|---|---|---|---|---|
| PIU | 2748 | 313 | 94 | 113 | 72 | 11 |
| % Con | 100 | 11.4 | 3.4 | 4.1 | 2.6 | 0.4 |

HCK (IC$_{50}$ > 200 μM)

| | CON | 10 | 50 | 75 | 100 | 200 |
|---|---|---|---|---|---|---|
| PIU | 1316 | 1286 | 1728 | 1415 | 1009 | 935 |
| % Con | 100 | 97.7 | 131.3 | 107.5 | 76.7 | 71.0 |

Compound D-58 (μM)

TREATMENT OF INFLAMMATION WITH 2,4,6-TRIHYDROXY-ALPHA-RHO-METHOXYPHENYLACETOPHENONE, OR ITS PHARMACEUTICALLY ACCEPTABLE DERIVATIVES

BACKGROUND OF THE INVENTION

The present invention is directed to the treatment of acute and chronic inflammatory responses, for example resulting from the presence of an allergen, injury, infection, etc. Allergic and acute inflammatory responses to injury, infection, or other tissue damage can set into motion a complex series of events. A variety of host cells that guard the host environment interface, including macrophages, mast cells, and epithelial/epidermal cells serve as the initiators of the inflammatory responses. These cells release various mediators during an inflammatory response, which include histamine, prostaglandins (PGs), leukotrienes (LTs) and proinflammatory cytokines (refs 1–4). These mediators have been implicated in the pathogenesis of a number of acute and chronic inflammatory conditions such as allergy, asthma, arthritis, psoriasis, and skin sunburn (refs 3–5).

The release of inflammatory agents is mediated by a cascade of intracellular signaling events which include activation of phosphoinositide turnover (ref 6), increase in cAMP levels (ref 7), activation of protein kinase C, and an increase in intracellular calcium levels and tyrosine phosphorylation of several cytosolic proteins (refs 7 and 8). Considerable efforts have been made for identification of chemical compounds that can interrupt these signaling events as potential anti-inflammatory agents (refs 9–12). However, the need for agents providing improved inhibition continues.

SUMMARY OF THE INVENTION

In accordance with the present invention, 2,4,6-trihydroxy-α-p-methoxyphenylacetophenone (also identified herein as "D-58"), or its pharmaceutically acceptable derivatives such as salt and ester forms, is administered for inhibiting inflammatory reactions to a subject in need thereof. The treatment can be remedial or prophylactic. Examples of the conditions that can be treated include acute as well as chronic inflammatory reactions and allergic inflammatory reactions, and specific examples include allergy, asthma, arthritis, psoriasis, skin sunburn, inflammatory pelvic disease, inflammatory bowel disease, urethritis, uvitis, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitis and cholangititis. The 2,4,6-trihydroxy-α-p-methoxyphenylacetophenone can be administered by one of a variety of routes as needed.

BRIEF DESCRIPTION OF THE DRAWINGS

The present invention will be described in conjunction with the accompanying drawings, in which.

DETAILED DESCRIPTION

The present invention is described in detail below. The present invention is not limited to the detailed aspects of this description, which should be considered exemplary rather than limiting.

The present invention is directed to the inhibition of inflammatory reactions in a subject, more particularly in a mammal, by the administration of 2,4,6-trihydroxy-α-p-methoxyphenylacetophenone or its pharmaceutically acceptable derivatives such as salt or ester forms. The invention is well-suited to treatment of humans. The 2,4,6-trihydroxy-α-p-methoxyphenylacetophenone may be administered orally or parenterally as needed. The treatment may be remedial or prophylactic (or both) in nature as needed. A prophylactic treatment means that the 2,4,6-trihydroxy-α-p-methoxyphenylacetophenone, or its pharmaceutically acceptable derivatives such as salt and ester forms, is administered to a subject that may encounter circumstances that might be expected to induce an inflammatory reaction in the subject. An example would be a person who expects to be exposed to a substance that provokes an allergic reaction. 2,4,6-trihydroxy-α-p-methoxyphenylacetophenone is a broad spectrum tyrosine kinase inhibitor with antioxidant activity (ref 13).

The inflammatory reactions treated in accordance with the present invention include acute and allergic inflammatory reactions. The allergic inflammatory reactions are caused by exposure of the subject to an allergen and include anaphylactic, IgE dependent, cytotoxic, immune-complex mediated and cell-mediated reactions. As shown in the examples below, 2,4,6-trihydroxy-α-p-methoxyphenylacetophenone is effective to inhibit inflammatory reactions by preventing IgE/antigen mobilization of calcium in mast cells and preventing mast cell degradation and $LTC_4$ release, without inhibition of plasma membrane calcium ATPase.

Acute inflammatory reactions treated by the method of the invention include responses to radiation, infection, chemicals, allergins, and injury. Examples of specific conditions that can be treated include allergy, asthma, arthritis, psoriasis, skin sunburn, inflammatory pelvic disease, inflammatory bowel disease, urethritis, uvitis, senusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitis, and cholangititis.

The 2,4,6-trihydroxy-α-p-methoxyphenylacetophenone (or its pharmaceutically acceptable derivatives) can be formulated as pharmaceutical compositions and administered to a mammalian subject, e.g. a human patient, in a variety of forms adapted to the subject and the specific condition being treated. Thus, the chosen route of administration may be oral or parenteral, i.e. by intravenous, intramuscular, topical or subcutaneous routes.

The 2,4,6-trihydroxy-α-p-methoxyphenylacetophenone (or its pharmaceutically acceptable derivatives) may be administered systemically, e.g., orally, in combination is with a pharmaceutically acceptable vehicle such as an inert diluent or an assimilable edible carrier, by injection, by inhalation or insufflation, topically, vaginally, rectally, by intracavitary administration, transdermally, intradermally, intraperitoneally or nasally.

It may be enclosed in hard or soft shell gelatin capsules, may be compressed into tablets, or may be incorporated directly with the food of the patient's diet. For oral therapeutic administration, it may be combined with one or more excipients and used in the form of ingestible tablets, buccal compositions, troches, capsules, elixirs, suspensions, syrups, wafers, and the like. It may be combined with a fine inert powdered carrier and inhaled by the subject or insufflated. Such compositions and preparations generally will contain at least 0.1% of 2,4,6-trihydroxy-α-p-methoxyphenylacetophenone (or its pharmaceutically acceptable derivatives). The percentage of the compositions and preparations may, of course, be varied and conveniently may be between about 2 to about 60% of the weight of a given unit dosage form. The amount of 2,4,6-trihydroxy-α-p-methoxyphenylacetophenone (or its pharmaceutically acceptable derivatives) in such therapeutically useful compositions is such that an effective dosage level will be obtained.

The tablets, troches, pills, capsules, and the like also may contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added as desired. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the 2,4,6-trihydroxy-α-p-methoxyphenylacetophenone (or its pharmaceutically acceptable derivatives) may be incorporated into sustained-release preparations and devices as desired or needed.

The 2,4,6-trihydroxy-α-p-methoxyphenylacetophenone (or its pharmaceutically acceptable derivatives) also may be administered intravenously or intraperitoneally by infusion or injection. Injectable solutions can be prepared in water, optionally mixed with a nontoxic surfactant. Dispersions also can be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the 2,4,6-trihydroxy-α-p-methoxyphenylacetophenone (or its pharmaceutically acceptable derivatives) adapted for the extemporaneous preparation of sterile injectable or infusible solutions or dispersions, optionally encapsulated in liposomes for example. In all cases, the ultimate dosage form is desirably sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the 2,4,6-trihydroxy-α-p-methoxyphenylacetophenone (or its pharmaceutically acceptable derivatives) in the required amount in the appropriate solvent with various of the other ingredients enumerated above, as required, followed by filter sterilization. In the case of sterile powders for the preparation of sterile injectable solutions, the methods of preparation include vacuum drying or freeze drying techniques, which yield a powder of the active ingredient plus any additional desired ingredient present in the previously sterile-filtered solutions.

For topical administration, it generally will be desirable to administer the 2,4,6-trihydroxy-α-p-methoxyphenylacetophenone (or its pharmaceutically acceptable derivatives) to the skin as compositions or formulations, in combination with a dermatologically acceptable carrier, which may be a solid or a liquid. Topical administration also may include administration vaginally, rectally, intracavitary and through the oral cavity. Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water-alcohol/glycol blends, in which the active agent can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions that can be used to deliver the 2,4,6-trihydroxy-α-p-methoxyphenylacetophenone (or its pharmaceutically acceptable derivatives) to the skin are found, for example, in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the 2,4,6-trihydroxy-α-p-methoxyphenylacetophenone (or its pharmaceutically acceptable derivatives) can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the 2,4,6-trihydroxy-α-p-methoxyphenylacetophenone (or its pharmaceutically acceptable derivatives) in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the 2,4,6-trihydroxy-α-p-methoxyphenylacetophenone (or its pharmaceutically acceptable derivatives) required for use in treatment will vary with the route of administration, the nature of the condition being treated and the age and condition of the patient. In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day. The 2,4,6-trihydroxy-α-p-methoxyphenylacetophenone (or its pharmaceutically acceptable derivatives) is conveniently administered in unit dosage form; for example, containing 5 to 1000 mg, conveniently 10 to 750 mg, most conveniently, 50 to 500 mg of active ingredient per unit dosage form. Ideally, the 2,4,6-trihydroxy-α-p-methoxyphenylacetophenone (or its pharmaceutically acceptable derivatives) should be administered to achieve peak plasma concentrations of from about 0.5 to about 75 mM, preferably, about 1 to 50 mM, most preferably, about 2 to about 30 mM. This may be achieved, for example, by the intravenous injection of a 0.05 to 5% solution, optionally in saline, or orally administered as a bolus containing about 1–100 mg of the 2,4,6-trihydroxy-α-p-methoxyphenylacetophenone (or its pharmaceutically acceptable derivatives). Desirable blood levels may be maintained by continuous infusion to provide about 0.01–5.0 mg/kg/hr or by intermittent infusions containing about 0.4–15 mg/kg of the 2,4,6-trihydroxy-α-p-methoxyphenylacetophenone (or its pharmaceutically acceptable derivatives).

The 2,4,6-trihydroxy-α-p-methoxyphenylacetophenone (or its pharmaceutically acceptable derivatives) conveniently may be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

EXAMPLES

The invention will now be illustrated by the following non-limiting Examples.

Reagents and Materials

Male Balb/c and female, 6–7 weeks old hairless albino mice (skh-1) were purchased from Charles River Laboratories (Wilmington, Mass.). Animals were caged in groups of five in a pathogen free environment in accordance with the rules and regulations of U.S. Animal Welfare Act, and National Institutes of Health (NIH). Animal care and the experimental procedures were carried out in agreement with institutional guidelines.

Fetal bovine serum was obtained from Hyclone (Logan, Utah). λ carrageenan, A23187, bovine serum albumin, Evans blue, dimethyl sulphoxide (DMSO) and formamide were purchased from Sigma (St. Louis, Mo.). Leukotriene (LT) $C_4$, Prostaglandin (PG) $E_2$ ELISA kits and fatty acid free bovine serum albumin (BSA) were from Cayman Company (Ann Arbor, Mich.). The preparation of dinitrophenyl (DNP)-BSA and monoclonal anti-DNP-IgE was carried out in accordance with previously-described techniques (refs 14 and 15 respectively). Ionomycin and thapsigargin were purchased from Calbiochem (La Jolla, Calif.).

Cell Culture

RBL-2H3 cells were maintained as monolayer cultures in 75- or 150-cm$^2$ flasks in Eagle's essential medium supplemented with 20% fetal calf serum (ref 16). HaCaT, a spontaneously transformed human epidermal cell line (ref 17), was maintained in Dulbecco's modified Eagle's medium (DMEM) supplemented with 10% fetal bovine serum.

Example 1

Synthesis of 2,4,6-Trihydroxy-α-p-Methoxyphenylacetophenone 2,4,6-Trihydroxy-α-p-methoxyphenylacetophenone (D-58) was synthesized according to the literature method (ref 13) by reacting phloroglucinol 1 with homoanisonitrile 2 followed by acid catalyzed hydrolysis of the synthetic intermediate 3 (see Scheme 1 below).

Characterization Data of Compound D-58 mp: 192–193.0° C.; $^1$H NMR (DMSO-$d_6$) δ 12.24 (br s, 2H), 10.40 (br s, 1H), 7.12 (d, J=9.0 Hz, 2H), 6.84 (d, J=9.0 Hz, 2H), 5.80 (s, 2H), 4.25 (s, 2H), 3.70 (s, 3H); $^{13}$C NMR (DMSO-$d_6$) δ 202.73, 164.86, 164.32, 157.90, 130.76, 127.86, 113.67, 103.78, 94.88, 55.20, 48.31; IR (KBr) 3074, 1614, 1595, 1082, 1051 cm$^{-1}$. MALDI-MS m/z 274.7 (M$^+$).

Example 2

Tyrosine Kinase Assays

Sf21 (IPLB-SF21-AE) cells derived from the ovarian tissue of the fall armyworm *Spodotera frugiperda*, were obtained from Invitrogen and maintained at 26–28° C. in Grace's insect cell medium supplemented with 10% FBS and 1.0% antibiotic/antimycotic (GIBCO-BRL). Stock cells were maintained in suspension at 0.2–1.6×10$^6$/ml in 600 ml total culture volume in 1 L Bellco spinner flasks at 60–90 rpm. Cell viability was maintained at 95–100% as determined by trypan blue dye exclusion.

Sf21 cells were infected with a baculovirus expression vector for BTK or SYK, as previously described (refs 18 and 19). Cells were harvested, lysed (10 mM Tris pH 7.6, 100 mM NaCl, 1% Nonidet P-40, 10% glycerol, 50 mM NaF, 100 mM Na$_3$VO$_4$, 50 μg/ml phenylmethylsulfonyl fluoride, 10 μg/ml aprotonin, 10 μg/ml leupeptin), and the kinase proteins were purified to homogeneity, as reported (refs 18 and 19).

For HCK kinase assays, HCK-transfected COS-7 cells were used. The cloning and expression of HCK in COS-7 cells has been described previously (ref 18). The pSV7c-HCK plasmid was transfected into 2×10$^6$ COS-7 cells using Lipofectamine (GIBCO/BRL), and the cells were harvested 48 hours later. The cells were lysed in NP-40 buffer and HCK was immunoprecipitated from the whole cell lysates with an anti-HCK antibody. Kinase assays were performed following a 1 hour exposure of the purified (BTK, SYK) or immunoprecipitated (HCK) tyrosine kinases to the test compound, as described in detail elsewhere (refs 18–22).

Following electrophoresis, kinase gels were dried onto Whatman 3M filter paper and subjected to phosphoimaging on a Molecular Imager (Bio-Rad, Hercules, Calif.) as well as autoradiography on film. Similarly, all chemiluminescent BTK and SYK Western blots were subjected to three dimensional densitometric scanning using the Molecular Imager and Imaging Densitometer using the Molecular Analyst/Macintosh version 2.1 software following the specifications of the manufacturer (Bio-Rad) (ref 18). For each drug concentration, a BTK or SYK kinase activity index was determined by comparing the ratios of the kinase activity in phosphorimager units (PIU) and density of the protein bands in densitometric scanning units (DSU) to those of the baseline sample and using the formula: Activity Index=[PIU of kinase band/DSU of BTK/SYK protein band]$_{test\ sample}$: [PIU of kinase band/DSU of BTK/SYK protein band]$_{baseline\ control\ sample}$.

Figure 1A:
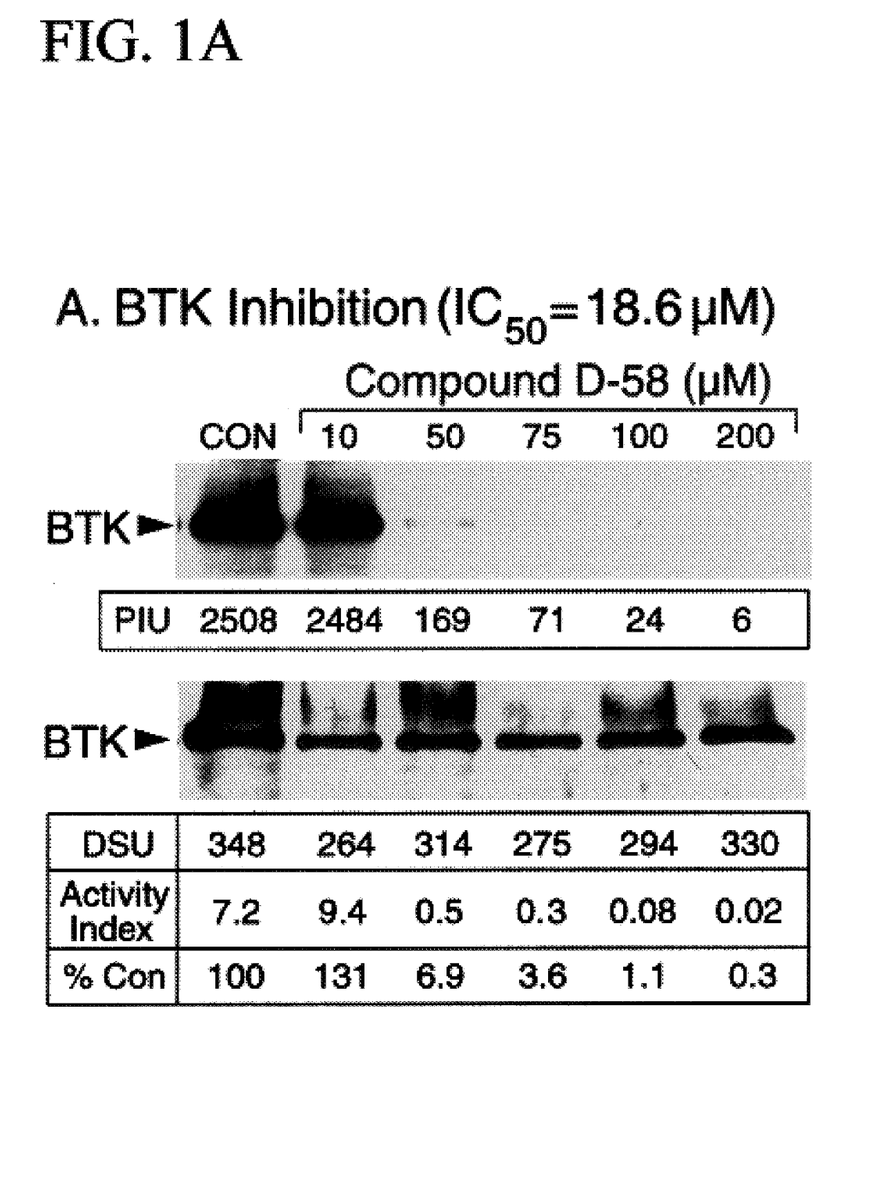
FIGS. 1A–C illustrate the tyrosine-kinase inhibition activity exhibited by 2,4,6-trihydroxy-α-p-methoxyphenylacetophenone.
Figure 1B:
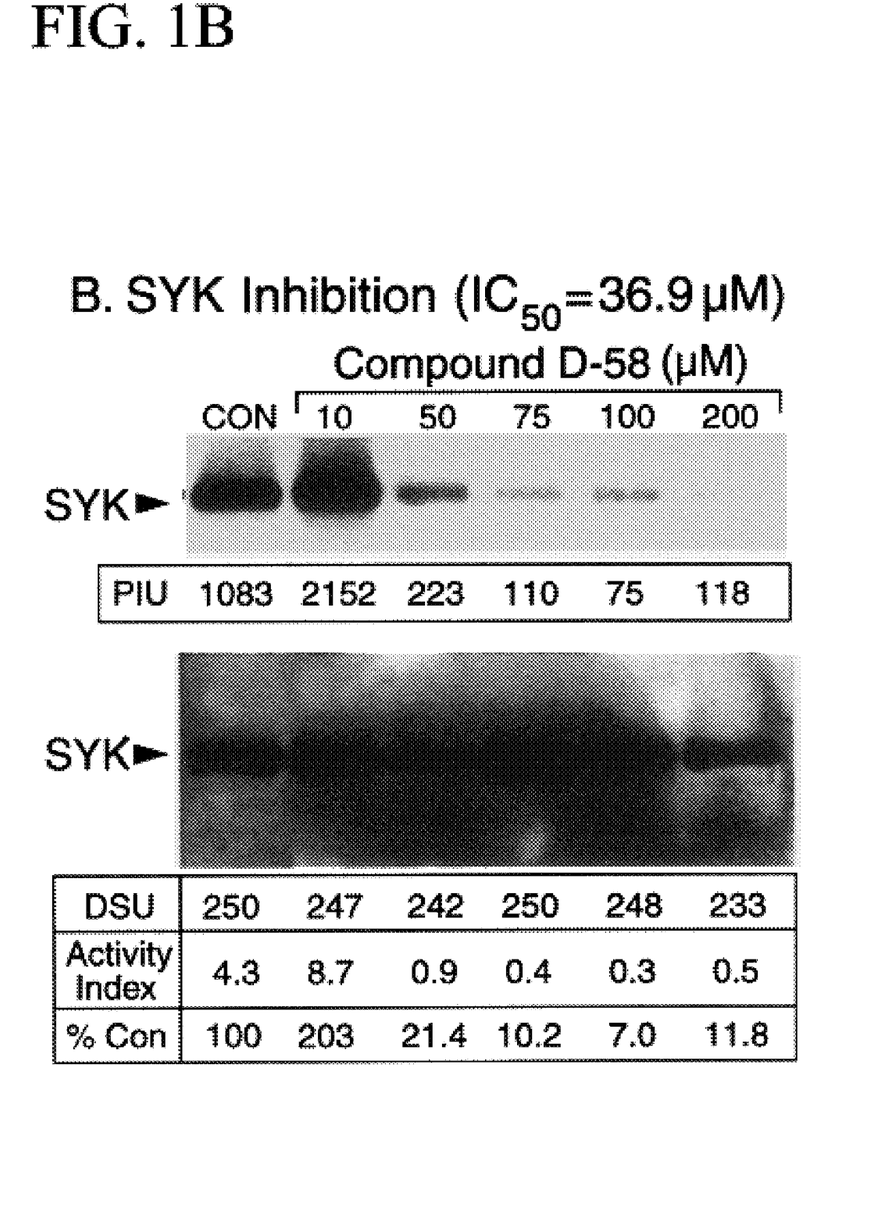
Figure 1C:
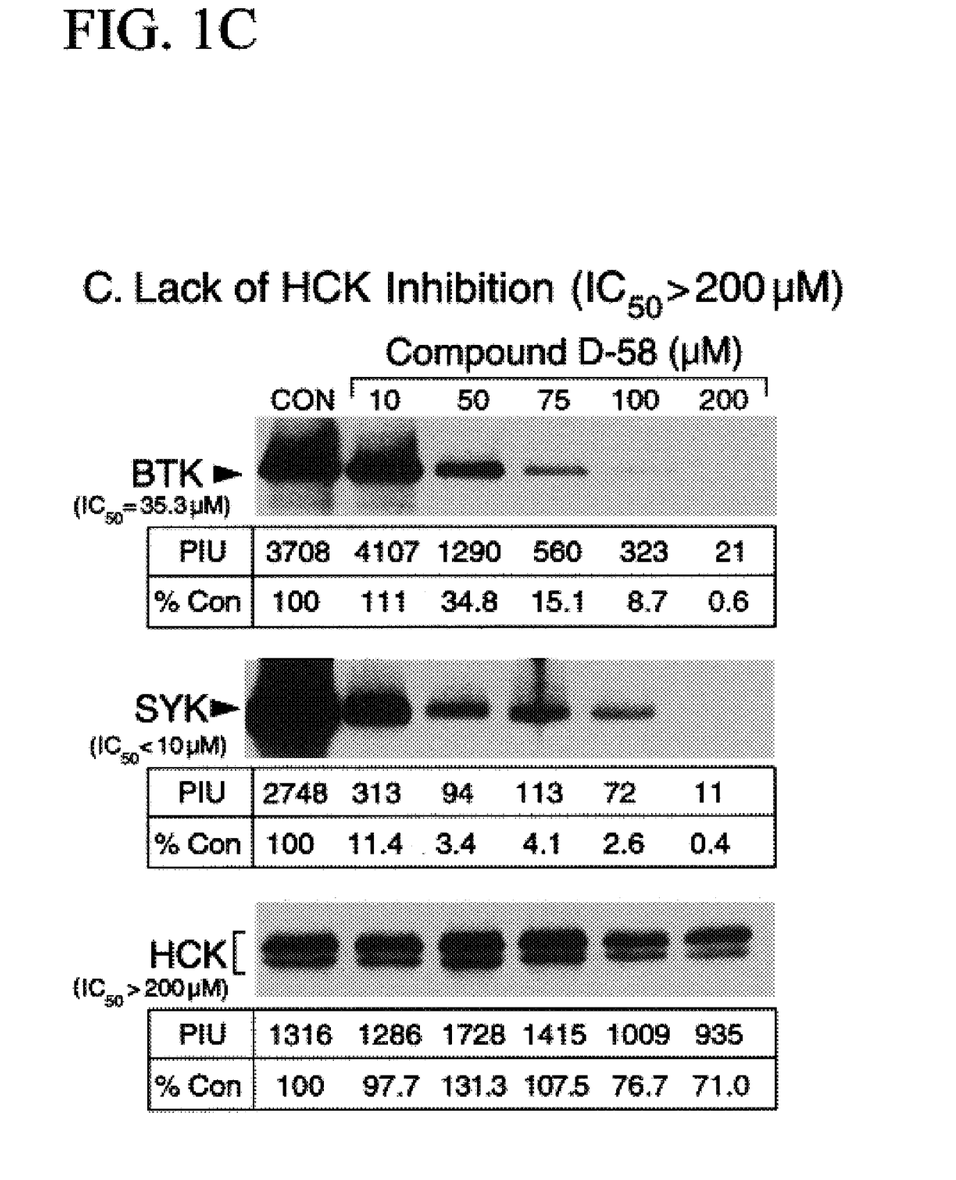

The results are shown in FIGS. 1A–C. It can be seen that Compound D-58 effectively inhibited the enzymatic activity of both BTK and SYK tyrosine kinases in a concentration-dependent fashion. In the first experiment, the measured IC$_{50}$ values were 18.6 μM for BTK (FIG. 1A) and 36.9 μM for SYK (FIG. 1B) tyrosine kinase. In the second experiment the IC$_{50}$ values were 35.5 μM for BTK and <10 μM for SYK (FIG. 1C). In contrast, compound D-58 did not inhibit the Src family tyrosine kinase HCK (IC$_{50}$>200 μM; FIG. 1C).

Example 3

IgE Receptor/Fc Epsilon RI-Mediated Mast Cell Activation and Mediator Release

Monolayers of RBL-2H3 rat mast cells were sensitized with monoclonal anti-DNP IgE antibody (0.24 mg/ml) for 1 hour at 37° C. in a 48-well tissue culture plate. Unbound IgE was removed by washing the cells with phosphate buffered saline. After washing, PIPES-buffered saline containing 1 mM calcium chloride was added to the monolayers of the RBL-2H3 cells. The cells were challenged with 20 ng/ml DNP-BSA for 30 minutes at 37° C. The plate was centrifuged at 200 g for 10 minutes at 4° C. and supernatants were saved. The RBL-2H3 cell monolayers were then washed with phosphate buffered saline, and solubilized in PIPES buffered saline containing 0.1% Triton X-100. β-hexosaminidase was estimated in cell free supernatants and Triton X-100 solubilized cells (ref 23).

Figure 2A:
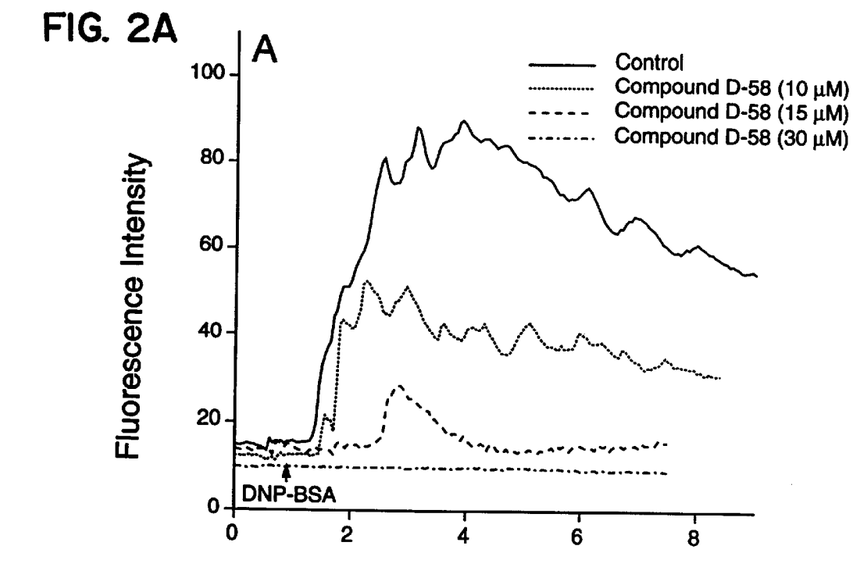
FIGS. 2A–B are graphs illustrating irreversible inhibition of Ca2+ mobilization in mast cells by 2,4,6-trihydroxy-α-p-methoxyphenylacetophenone.

To study the effects of compound D-58, RBL-2H3 cells were incubated with compound D-58 at the indicated concentrations or vehicle for 1 hour prior to antigen challenge. Mast cell degranulation (β-hexosaminidase release, % of total) was assessed by measuring the β-hexosaminidase levels in cell free supernatants and Triton X-100 solubilized pellets using the formula: 3-hexosaminidase release, % of total=100×(β-hexosaminidase level in supernatant/β-hexosaminidase level in supernatant+solubilized pellet). LTC$_4$ levels in cell free supernatants of mast cells were estimated using standard procedures (ref 24). To summarize, RBL-2H3 cells were sensitized with IgE, loaded with calcium indicator (Fluo-3), and then processed for calcium imaging as after challenge with agonists as described in Materials and Methods. FIG. 2A shows concentration dependent inhibition of IgE/antigen induced calcium mobilization by compound D-58 in mast cells. To study the effect of compound D-58, RBL-2H3 cells were incubated with indicated concentrations of compound D-58 for 20 minutes prior to stimulation.

Figure 2B:
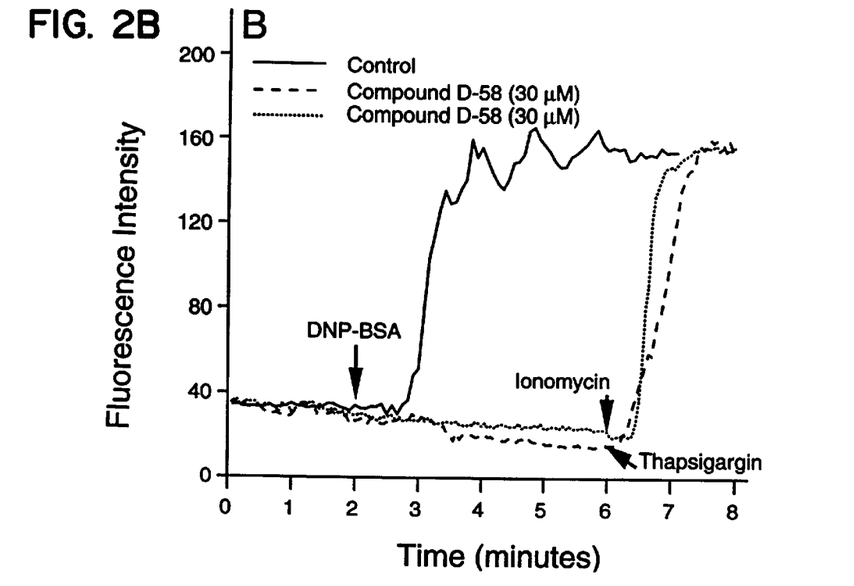

The results are shown in FIGS. 2A–B. IgE/antigen stimulation of RBL-2H3 mast cells activates a cascade of signal transduction events, which includes tyrosine phosphorylation of several proteins and SYK/BTK-mediated activation of phospholipase C, which generates second messengers inositol 1,4,5-triphosphate (IP$_3$) and 1,2-diacylglycerol (DAG) (ref 7). The binding of IP$_3$ to its receptors releases calcium from endoplasmic reticulum calcium stores (ref 7). Since compound D-58 is a potent inhibitor of SYK and BTK tyrosine kinases, it can prevent IgE/antigen induced SYK/BTK-dependent calcium mobilization in mast cells. IgE sensitized and Ca$^{2+}$ indicator fluo-3/AM loaded RBL-2H3 cells were stimulated with 20 ng/ml antigen (DNP-BSA) in presence of 1 mM calcium chloride and the fluorescence intensity, reflecting the calcium ion concentration was measured. The intracellular calcium ion concentration reached a maximum within 1–2 minutes after stimulation (FIG. 2A), which is consistent with previous findings (ref 23). The frequency of calcium oscillation varied from cell to cell with an average of 1.6±0.1 cycles/s (mean±SEM; n=21). Compound D-58 inhibited the calcium response in a concentration-dependent fashion with abrogation of calcium mobilization at 30 μM (FIG. 2A). Thus, compound D-58 effectively prevents IgE/antigen-induced calcium mobilization in mast cells, which is consistent with its inhibitory effects on SYK and BTK tyrosine kinases.

An alternative mechanism for the cells to maintain low cytosolic calcium levels is the activation of cell plasma membrane calcium ATPase or calcium pump (refs 32 and 33). Therefore, the effect of compound D-58 on ionophore and thapsigargin induced calcium mobilization also was studied. Ionomycin takes extracellular calcium inside the cells, and bypasses most of the signal transduction events, whereas thapsigargin inhibits endoplasmic reticulum calcium pump, and selectively depletes IP$_3$-sensitive storage resulting in an increase in the cytosolic calcium levels (ref 33). In summary, IgE-sensitized RBL-2H3 cells were treated with 30 μM compound D-58 for 20 minutes and challenged with DNP-BSA (20 ng/ml). The cells were then stimulated with either ionomycin (1 μM), or thapsigargin (2 μM). The results are shown in FIG. 2B. The arrows indicate the time points at which the cells were exposed to the agents.

Compound D-58 did not inhibit calcium responses induced by 1 µM iomomycin or 2 µM thapsigargin (FIG. 2B). Therefore, the plasma membrane calcium pump in IgE/antigen challenged mast cells does not appear to be affected by compound D-58.

Example 4

Measurement of IgE/DNP-BSA Triggered $Ca^{2+}$ Signals in Mast Cells

The fluorescent $Ca^{2+}$ indicator, fluo-3/AM (Molecular Probes) was used to detect $Ca^{2+}$ mobilizations in individual cells (ref 25). Briefly, the IgE sensitized monolayers of mast cells were incubated with 1 µM fluo-3/AM at 37° C. for 30 minutes. After incubation the cells were washed twice and 1 ml PIPES buffer was added to the wells. The plate was then mounted onto an inverted microscope (Nikon ECLIPSE TE300) which was linked to a calcium imaging device (Universal Imaging Co., West Chester, Pa.). The excitation and emission wavelengths were 485 and 535 nm respectively. The fluorescent images of the cells were acquired by using a CCD72 video camera (Dage-MTI, Inc., Michigan City, Ill.) set at a speed of 1 frame/3s and digitized by computer. After 1 minute of image acquisition, 20 µl of 1 µg/ml DNP-BSA, 11 µg/ml ionomycin, or 20 µg/ml thapsigargin was added into the well to stimulate the cells. In order to study the effects of compound D-58 on the calcium mobilizations, the cells were exposed to compound D-58 20 minutes prior to, or 2 minutes after the addition of the agonist. The image acquisition and fluorescence intensity analysis were controlled by the software MetaFluor (Universal Imaging Co.). The background fluorescence was subtracted from each image.

In order to examine the effects of compound D-58 on IgE receptor/FcεRI-mediated mast cell activation and mediator release, RBL-2H3 mast cells were exposed to increasing concentrations of this ethanone or vehicle prior to challenge with antigen (DNP-BSA). To summarize, RBL-2H3 cells were sensitized with monoclonal anti-DNP IgE, treated with compound D-58 or vehicle, and then challenged with DNP-BSA. Mast cell β-hexosaminidase release (FIG. 3A) and $LTC_4$ release (FIG. 3B) were measured. Hexosaminidase release is expressed as percent release of total cellular content. $LTC_4$ release is expressed as percent of maximum control release from vehicle treated control mast cells. The data points represent the mean ±SEM values obtained from 3–6 independent experiments. *P<0.01 compared to control was determined by Student's t test. *P<0.05 and **P<0.0001 compared to vehicle-treated controls were determined by Student's t test.

Figure 3A:
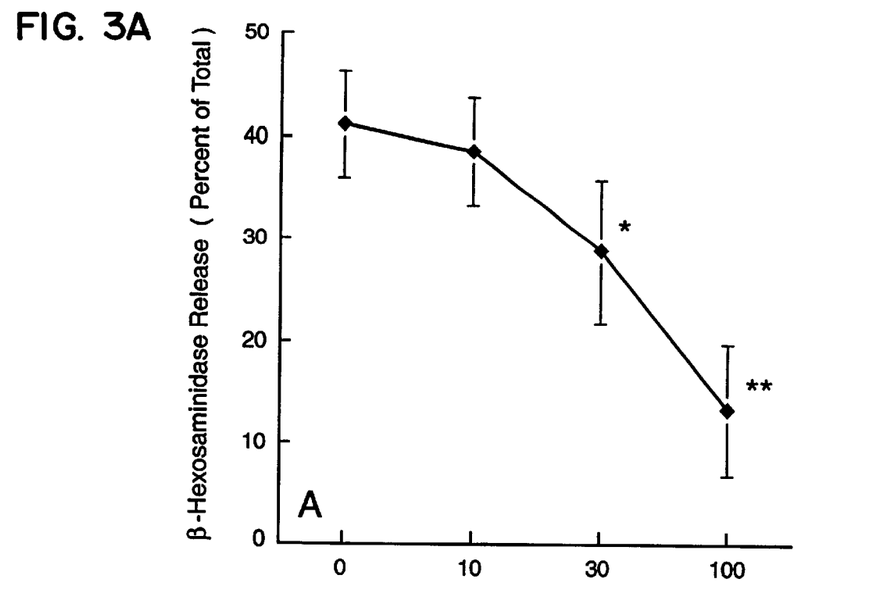
FIGS. 3A–B are graphs illustrating inhibition of IgE receptor/Fc Epsilon RI-mediated mast cell mediator release by 2,4,6-trihydroxy-α-p-methoxyphenylacetophenone.
Figure 3B:
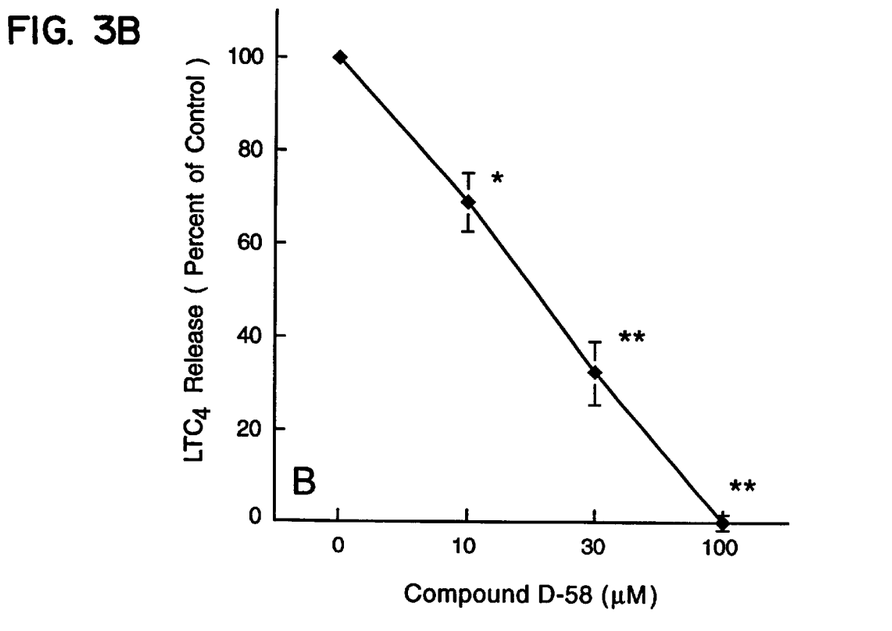

Compound D-58 did not affect the viability of RBL-2H3 cells even at a 300 µM concentration (2 hour treatment at 37° C.), as assessed by trypan blue dye exclusion. The viability of compound D-58-treated mast cells ranged from 91 to 92%. Incubation of RBL-2H3 cells with compound D-58 did not induce mediator release (data not shown). Stimulation of RBL-2H3 mast cells using IgE/antigen as a stimulus induced the release of significant amounts of preformed granule-associated B-hexosaminidase (47.2±7.9% of total cellular content) as well as newly synthesized $LTC_4$ (5.8±1.8 µg/$10^6$ cells). As shown in FIG. 3, compound D-58 inhibited the IgE/antigen induced mast cell degranulation (β-hexosaminidase) (FIG. 3A) and $LTC_4$ release (FIG. 3B) in a concentration-dependent fashion.

Example 5

Passive Cutaneous Anaphylaxis

The in vivo biologic activity of compound D-58 was examined in a well characterized murine model of passive cutaneous anaphylaxis. In order to induce passive cutaneous anaphylaxis, left ears of Balb/c mice were sensitized with 50 µg DNP-IgE intradermally. Right ears were injected with equal volumes of saline. Dorsal sides of the ears of Balb/c mice were injected intradermally with 50µg of DNP-IgE (left ears) or PBS (right ears) using a 30-gauge needle (ref 28). Twenty hours later, mice were challenged with 100 µg antigen (DNP-BSA) in 200 µl 2% Evans blue dye intravenously. Control mice were given PBS (but not antigen) intravenously with 2% Evans blue. For quantitation of Evans blue dye extravasation as a measure of anaphylaxis-associated vascular hyperpermeability, 8 mm² skin specimens were removed from the ears of mice, minced in 2 ml formamide and incubated in a 80° C. water bath for 2 hours to extract the dye. The absorbance was read at 570 nm using a spectrophotometer.

For assessment of the vascular leak, animals were sacrificed 30 minutes after the antigen challenge. The plasma exudation was assessed by quantitation of the amount of Evan's blue dye extravasated into the ear skin 30 minutes after the antigen challenge. When vehicle-treated mice were challenged with antigen, high levels of Evan's blue dye extravasation was observed in the DNP-IgE-injected ears (Absorbance at 570 nm =0.64±0.08).

To summarize, the effects of compound D-58 on anaphylaxis-associated vascular hyperpermeability were examined by evaluating the cutaneous extravasation of Evans blue dye in mice. In order to examine the effects of compound D-58 on passive cutaneous anaphylaxis, a group of mice were treated with D-58 (25 mg/kg i.p.) twice at 1 hour intervals prior to the antigen challenge. The absorbance data points were calculated as the mean ±SEM values (n=5 mice).

Figure 4:
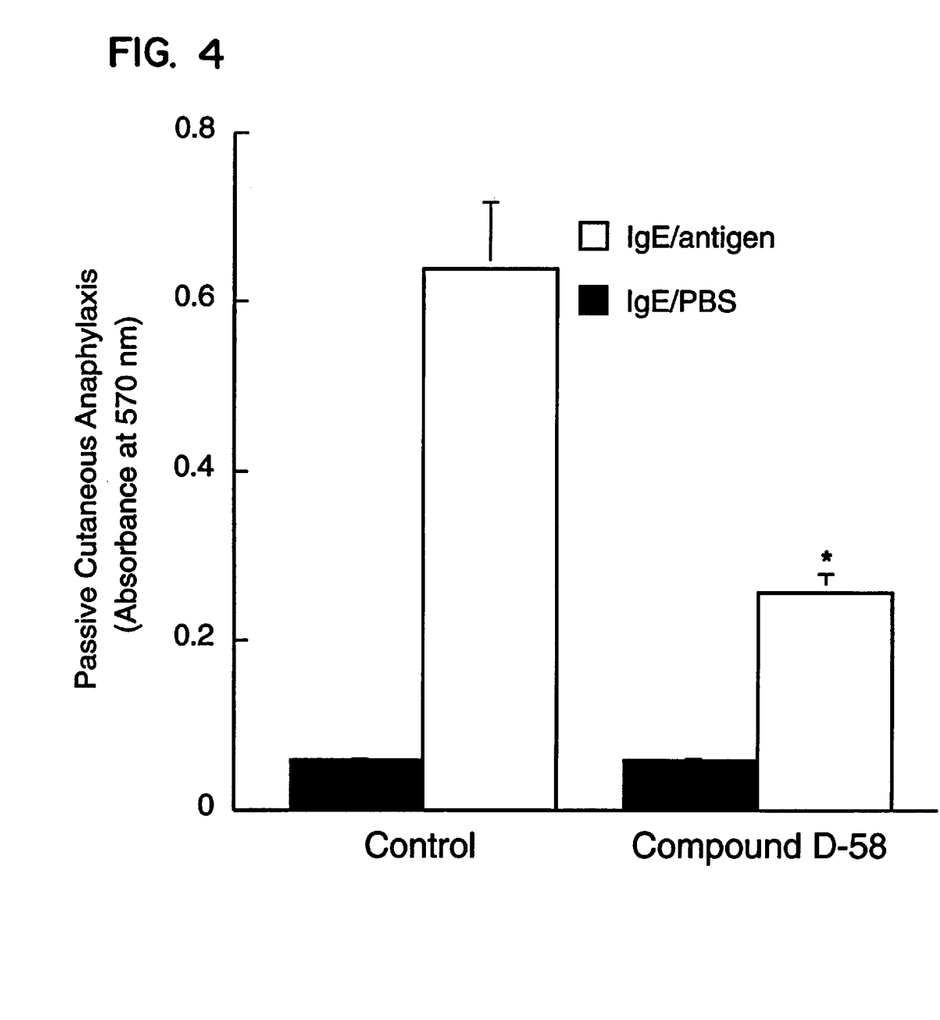
FIG. 4 is a graph illustrating inhibition of IgE-dependent passive cutaneous anaphylaxis in mice by 2,4,6-trihydroxy-α-p-methoxyphenylacetophenone.

As seen from the results shown in FIG. 4, treatment of mice with compound D-58 prior to antigen challenge significantly reduced the dye extravasation in their DNP-IgE injected ears (Absorbance at 570 nm=0.26±0.02; p<0.05 compared to vehicle-treated controls was determined by Student's t test). These data demonstrate that compound D-58 effectively prevented cutaneous anaphylaxis in mice, which is consistent with its ability to inhibit mast cell mediator release.

Example 6

Stimulation of HaCaT Cells with UVB and Prostaglandin $E_2$ Assay

A bank of 8-FSX24T12/HO/UVB lamps (National Biological Corporation, Twinsburg, Ohio) that emit light predominantly in the UVB range (280–320 nm) was used to irradiate the cell cultures. The performance of the UVB lamps was always confirmed before irradiation using a UVB meter (model-500C obtained from National Biological Corporation, Twinsburg, Ohio). The dose of UVB light used to irradiate cell cultures was 20 mJ/cm². Confluent HaCaT cells cultured in 24-well culture dishes were washed three times with serum-free DMEM containing 1% BSA and incubated with indicated concentrations of compound D-58 for 1 hour at 37° C. After incubation, the cells were washed twice with PBS, exposed to 20 mJ/cm² UVB light, and resuspended in serum-free DMEM containing 1% BSA. Compound D-58 was readministered after irradiation and the cells were incubated for another 24 hours at 37° C. The cell supernatants were collected and their $PGE_2$ concentration was measured by ELISA. The protein contents of the cell pellets were determined using the Pierce BCA protein assay method.

One of the major arachidonic acid metabolites in UVB-irradiated epidermal cells is prostaglandin $E_2$ ($PGE_2$), which induces edema and erythema in skin (refs 34 and 35). $PGE_2$ release can be detected as early as 6 hours and peaks between 24–48 hours following UVB exposure. The effect of compound D-58 on $PGE_2$ release by UVB-irradiated epidermal cells was examined. The human epidermal cell line, HaCaT was exposed to UVB light, incubated in the presence or absence of compound D-58 and the cumulative amounts of $PGE_2$ released into cell supernatants by 24 hours post irradiation were determined.

To summarize, confluent monolayers of the human epidermal cell line HaCaT were either irradiated with UVB (20 $mJ/cm^2$) or sham irradiated. In order to study the effect of compound D-58, cells were incubated with indicated concentrations of compound D-58 for 1 hour prior to irradiation. The drug was readministered after UVB exposure. Cumulative $PGE_2$ release during a 24 hours incubation was determined by measuring the $PGE_2$ content of cell free supernatants using EIA. Total cellular proteins were estimated in cell pellets after removal of supernatants. The results are expressed as $PGE_2$ pg/µg of cellular protein. The data points represent the mean ±SEM values (n=3). *p<0.0001 compared to vehicle-treated controls was determined by Student's t test.

Figure 5:
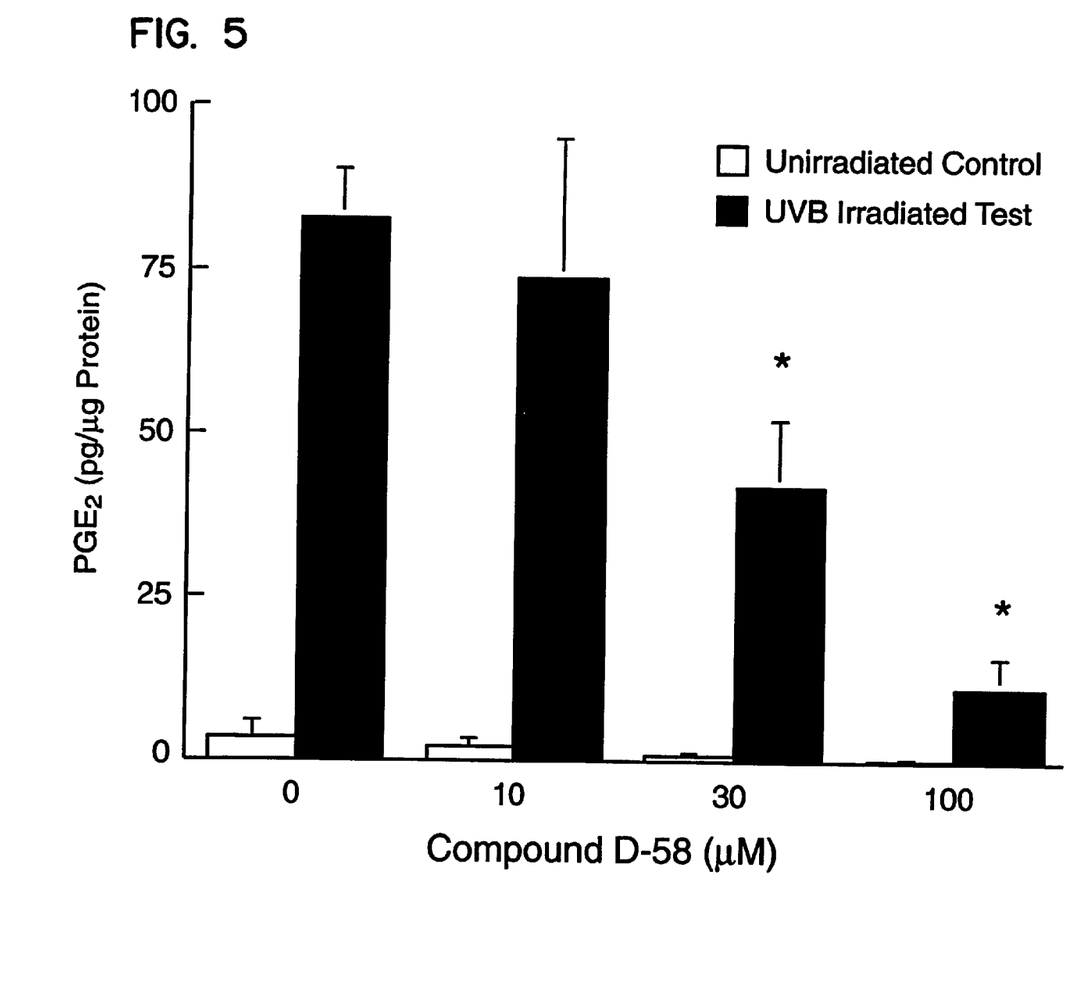
FIG. 5 is a graph illustrating in vitro inhibition of Prostaglandin $E_2$ release from UVB-irradiated HaCaT cells by 2,4,6-trihydroxy-α-p-methoxyphenylacetophenone.

As shown in FIG. 5, the exposure of HaCaTs to 20 $mJ/cm^2$ UVB induced a 25-fold increase in $PGE_2$ level at 24 hours post irradiation (82.4±7.76 vs 3.65±2.72 pg/µg protein, p<0.0001). Treatment with compound D-58 inhibited the $PGE_2$ release from UVB irradiated cells in a concentration-dependent fashion.

Example 7

In Vivo Inhibition of $PGE_2$ Release by Compound D-58

The effects of compound D-58 on $PGE_2$ release in vivo were examined using a well characterized air pouch mouse model of acute inflammation (ref 36). An acute inflammatory response was induced in the air pouches of mice by the injection of carrageenan, a sulfated polysaccharide obtained from the alga *Chondrus crispus* (ref 36).

Balb/c (6–8 weeks old male) mice were utilized for these experiments. To create an air pouch, mice were injected with 3 ml sterile air subcutaneously using a 30 gauge needle on days 0 and 3 as described previously (refs 30 and 31). Six days after the initial injection of air, mice were injected with 2 ml of 1% carrageenan into the subcutaneous air pouch.

In order to study the effect of compound D-58, a group of mice was injected with the drug i.p. 60 minutes and 30 minutes before the carrageenan challenge. Control mice were treated with vehicle alone. After 4 hours of challenge with carrageenan, mice were sacrificed and the contents of the air pouches were harvested by lavage with 2 ml cold saline. The recovered fluids were centrifuged at 250×g for 15 minutes at 4° C. Supernatants were saved at −80° C. for the estimation of the of prostaglandin $E_2$ contents. $PGE_2$ levels in pouch fluids were estimated by ELISA, as described earlier (ref 26).

Figure 6:
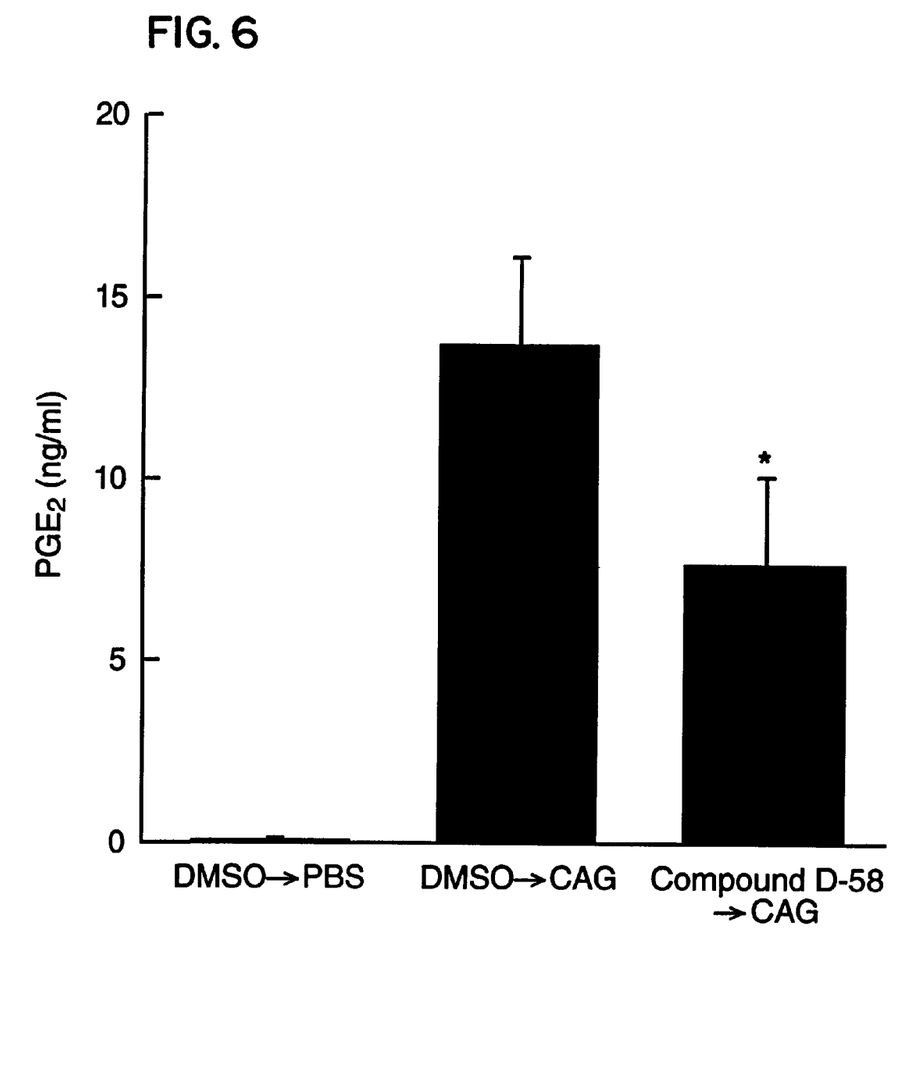
FIG. 6 is a graph illustrating in vivo inhibition of $PGE_2$ release by 2,4,6-trihydroxy-α-p-methoxyphenylacetophenone.

The results are expressed as ng/ml $PGE_2$ in lavage fluid as shown in FIG. 6. The data points represent the mean ±SEM values (n=4–5 mice). *p<0.05 compared to vehicle-treated controls was determined by Student's t test.

As shown in FIG. 6, pretreatment of mice with 50 mg/kg compound D-58 twice before carrageenan challenge decreased the $PGE_2$ release into the air pouch by approximately 50%.

Example 8

Inhibition of Acute Inflammatory Responses of UVB-Irradiated Skin

Irradiation Procedure

Mice (skh-1) were treated daily with 20 mg/kg i.p. bolus injections of compound D-58 from day −2 (i. e. 2 days prior to UVB exposure) until the termination of the experiment. Anesthetized mice received UVB radiations to a 2.0 $cm^2$ area on their dorsal surface. This area was painted either with the test compound (1.5 $mg/cm^2$) in drug receiving mice, or with vehicle in control mice 15 minutes before irradiation. The distance between UVB lamps and surface receiving irradiation was 20 cm. The final radiation dose received by skh-1 hairless mice was 180 $mJ/cm^2$ which is approximately four times higher than the minimal erythema dose (MED) (ref 29) in these mice.

Skin Edema Measurement

Skinfold thickness of the back of the mice was recorded prior to, and on each day after UVB exposure for five days with a digital thickness gauge (Mitutoyo Co., Plainfield, N.J.) which measures the skinfold thickness in a 0–10 mm range with an accuracy of 0.015 mm.

Figure 7:
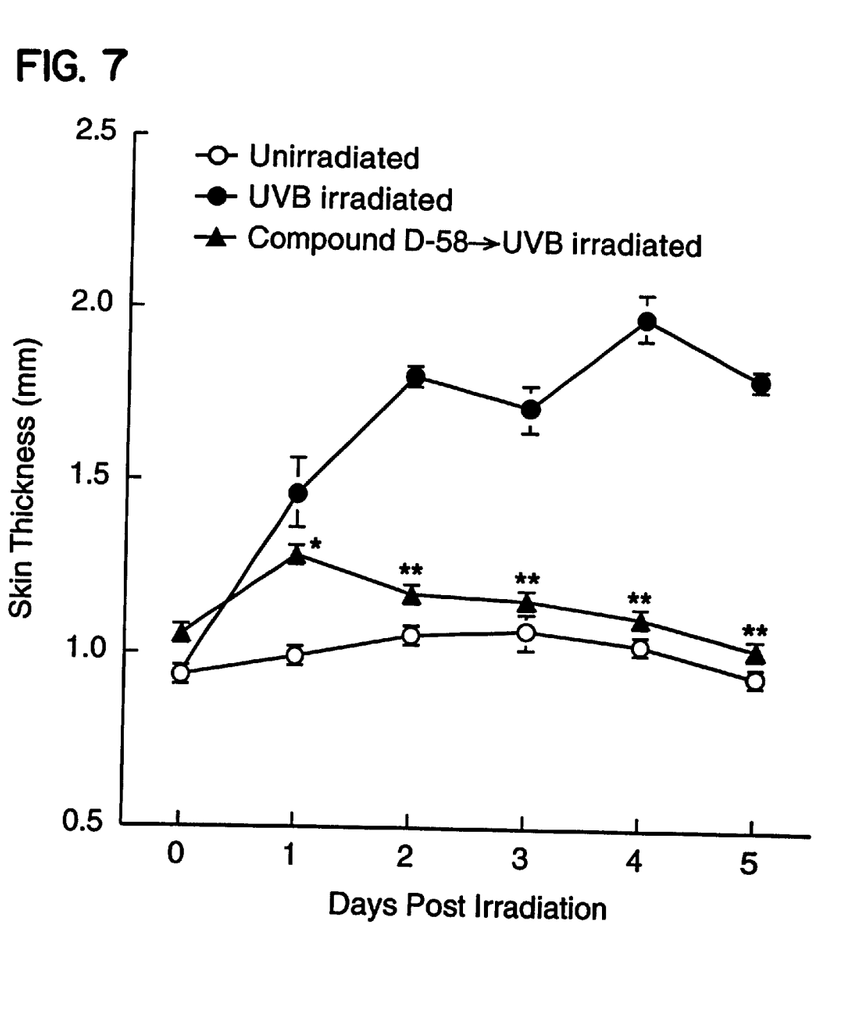
FIG. 7 is a graph illustrating inhibition of acute inflammatory responses of UVB-irradiated skin in skh-1 mice.

An acute UVB exposure of skin causes "sunburn" with histopathological changes including tissue necrosis, hemorrhage, edema and infiltration of leukocytes (ref 37). Arachidonic acid metabolites such as leukotrienes and prostaglandins contribute to these histopathological changes (refs 4, 5, 35). It was investigated whether compound D-58 could attenuate skin sunburn following UV irradiation in vivo. For this purpose female, hairless, albino skh-1 mice were exposed to 180 $mJ/cm^2$ UVB light and their skinfold thickness, as a parameter of acute inflammation, was measured on days 1 through 5 following irradiation. The data are shown in FIG. 7, where skin fold thickness is expressed in millimeters (mm). The data points represent the mean ±SEM values (n=5 mice). *p<0.05 and **p<0.001 compared to vehicle-treated UVB irradiated controls were determined by Student's t test.

FIG. 7 shows that a single exposure to 180 $mJ/cm^2$ UVB induced a time dependent increase in skinfold thickness. Treatment of mice with compound D-58 effectively inhibited the development of skin edema after UVB exposure. By 72 hours post irradiation, the skinfold thickness in drug-treated mice was at baseline control levels. In contrast, the skin thickness of the vehicle-treated control mice remained abnormal throughout the five day observation period.

Example 9

Histological Studies of Skin

After mice from Example 7 were sacrificed electively, a skin specimen was removed and spread on a sheet of dental wax. An 8 $mm^2$ biopsy punch was taken and fixed in buffered formalin. 4–5 µm thick sections were cut from paraffin blocks. In order to study the histopathological changes in skin following UVB exposure, the tissue sections were stained with hematoxylin and eosin and the stained slides were examined microscopically.

Figure 8A:
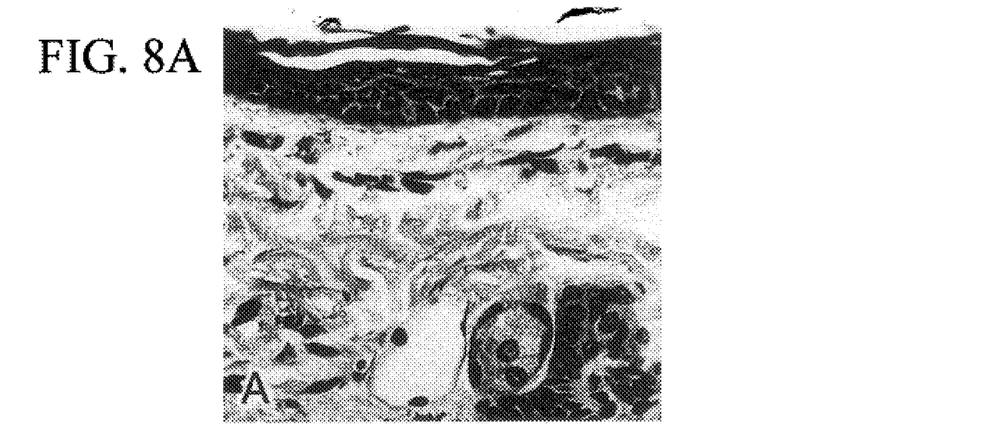
FIGS. 8A–C illustrate the effects of 2,4,6-trihydroxy-α-p-methoxyphenylacetophenone on UVB-induced histological changes in skin.
Figure 8B:
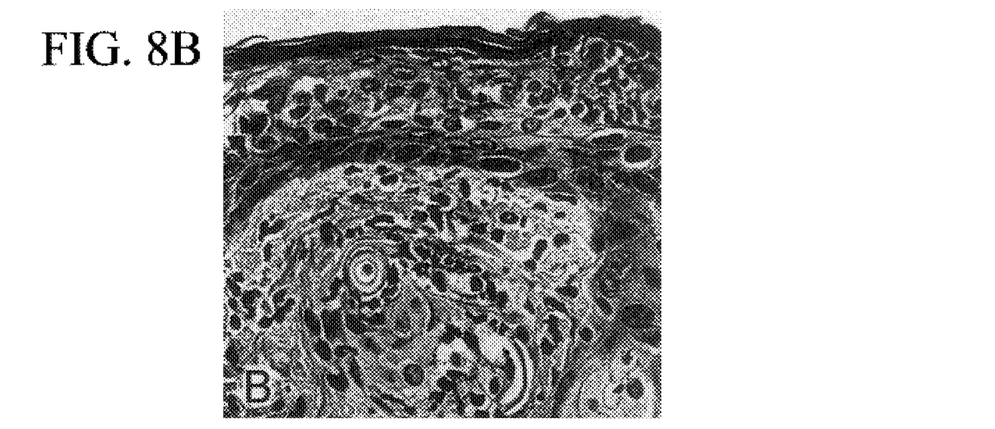
Figure 8C:
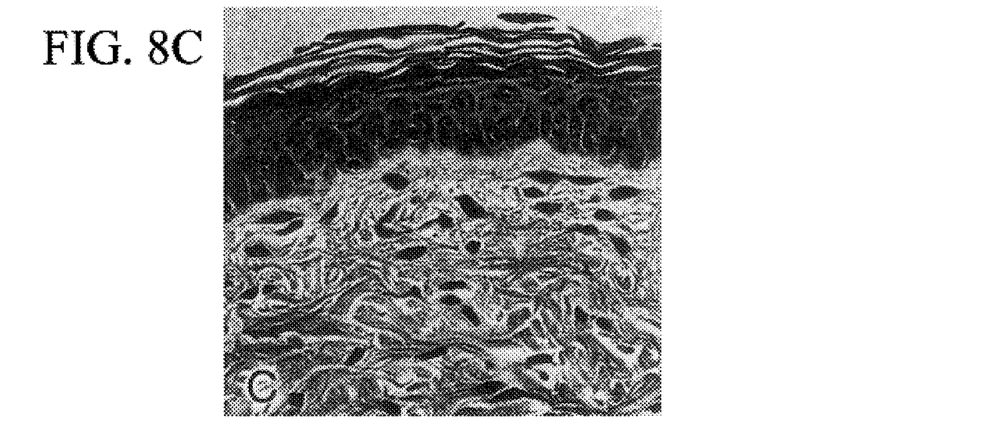

The effects of compound D-58 on UVB-induced histological changes in skin were examined and the results are illustrated in the 40×magnifications of FIGS. 8A–8C. The normal epidermis typically has a 2–3 cell layer and contains scattered inflammatory cells especially around hair follicles (FIG. 8A). The UVB-irradiated skin showed thickened epidermis with 3–5 cell layers. Large numbers of neutrophils also were accumulated in the dermis (FIG. 8B). In contrast, the skin of mice treated with compound D-58 looked very much like the skin of unirradiated controls (FIG. 8C), with 1–2 cell layers of epidermis and normal dermis. Thus, compound D-58 prevented the development of edema and neutrophil influx in UVB irradiated skin of mice.

The results of the experiments described above evidence that 2,4,6-trihydroxy-α-p-methoxyphenylacetophenone) has potent anti-allergic and anti-inflammatory properties. The ability of this compound and its pharmaceutically acceptable derivatives to inhibit the release of proinflammatory mediators from activated mast cells and UVB-irradiated epidermal cells and its in vivo activity profile in murine models of allergy and inflammation support the use of this agent in treatment programs for severe allergic as well as other inflammatory disorders.

Numerous references are included herein and listed below. The disclosures of these references are incorporated herein by reference, as if fully set forth.

While a detailed description of the invention has been provided above, the description should be considered exemplary and illustrative rather than limiting, and various modifications not departing from the spirit and scope of the invention will be apparent to those skilled in the art. The invention is not limited to the above detailed description, but is defined by the following claims.

REFERENCES

1. Barnes, P. J. 1998. Pathophysiology of Allergic Inflammation in Allergy, 5th Edition, Vol I. E. Middleton, C. E. Reed, E. F. Ellis, N. F. Adkinson, J. W. Yingers, and W. W. Busse, eds., Mosby-Year Book Inc., St. Louis, Mo., p. 356–365.
2. Malaviya, R., R. Malaviya, and B. A. Jakschik. 1993. Reversible translocation of 5-lipoxygenase in mast cells upon IgE/antigen stimulation. *J. Biol. Chem.* 268:4939.
3. Humes, J. L., S. Sadowski, and Galvage, M. 1978. Evidence for two sources of arachidonic acid for oxidative metabolism by mouse peritoneal macrophages. *J. Biol. Chem.* 257:1.
4. Galli, S. J. 1993. New concepts about the mast cells. *New Eng. J. Med.* 328:257.
5. Malaviya, R. and S. N. Abraham. 1998. Clinical Implications of mast cell-bacteria interaction. *J. Mol. Med.* 76:617.
6. William S. L. 1992. Prostanoid biosynthesis and mechanism of action *Am. J. Physiol.* 263:F181.
7. Hamawy, M. J., S. E. Mergenhagen, and R. P. Siraganian. 1995. Protein tyrosine phosphorylation as a mechanism of signalling in mast cells and basophils. *Cellular Signalling,* 7:535.
8. Scharenberg, A. M. and J. P. Kinet. 1995. Early events in mast cell signal transduction. *Chem. Immunol.* 61:72.
9. Lepley, R. A., D. T. Muskardin and F. A. Fitzpatrick. 1996. Tyrosine kinase activity modulates catalysis and translocation of cellular 5-lipoxygenase. *J. Biol. Chem.* 271:6179.
10. Oliver, J. M., D. L. Burg, B. S. Wilson, J. L. McLaughlin, and R. L. Geahlen. 1994. Inhibition of mast cell FceR1-mediated signalling and effector function by the syk-selective inhibitor, Piceatannol. *J. Biol. Chem.* 269:29697.
11. Chanmugam, P., L. Feng, S. Liou, B. C. Jang, M. Boudreau, G. Yu, J. H. Lee, H. J. Kwon, B. Teruhiko, M. Yoshida, Y. Xia, C. B. Wilson, and D. Hwang. 1995. Radicicol, a protein tyrosine kinase inhibitor, suppresses the expression of mitogen-inducible cyclooxygenase in macrophages stimulated with lipopolysaccharide and in experimental glomerulonephritis. *J. Biol. Chem.* 270:5418.
12. Levitzki, A. and A. Gazit. 1995. Tyrosine kinase inhibition: an approach to drug development. *Science* 267:1782.
13. Trieu, V. N., Y. Dong, Y. Zheng, and F. M. Uckun. 1999. In vivo antioxidant activity of genistein in a murine model of singlet oxygen-induced cerebral stroke. *Radiation Res.* 152:508.
14. Wei, Y., K. Heghinian, R. L. Bell, and B. A. Jakschik. 1986. Contribution of macrophages to immediate hypersensitivity reaction. *J. Immunol.* 137:1993.
15. Liu, F. T., J. W. Bohn, E. L. Ferry, H. Yamamoto, C. A. Molinaro, L. A. Sherman, N. R. Klinman, and D. H. Katz. 1980. Monoclonal dinitrophenyl-specific murine IgE antibody: preparation, isolation, and characterization. *J. Immunol.* 124:2728.
16. M. J. Hamawy, S. E. Mergenhagen and R. P. Siraganian. 1995. Protein tyrosine phosphorylation as a mechanism of signalling in mast cells and basophils. *Cellular Signalling.* 7:535.
17. Malaviya, R., A. R. Morrison, and A. P. Pentland. 1996. Histamine in human epidermal cells is induced by ultraviolet light injury *J. Invest. Dermatol.* 106:785.
18. Mahajan, S., S. Ghosh, E. A. Sudbeck, Y. Zheng, S. Downs, M. Hupke, and F. M. Uckun, 1999. Rational design and synthesis of a novel anti-leukemic agent targeting Bruton's Tyrosine Kinase (BTK): LFM-A13 [a-cyano-b-hydroxy-b-methyl-N-(2,5-dibromophenyl) propenamide]. *J. Biol. Chem.* 274:9587.
19. Sudbeck, E. A., X. -P. Liu, R. K. Narla, S. Mahajan, S. Ghosh, C. Mao, and F. M. Uckun. 1999. Structure-based design of specific inhibitors of janus kinase 3 as apoptosis-inducing anti-leukemic agent. *Clin. Cancer Res.* 5:1569.
20. Uckun, F. M., K. G. Waddick, S. Mahajan, X. Jun, M. Takata, J. Bolen, and T. Kurosaki. 1996. Bruton's tyrosine kinase as a mediator of radiation-induced apoptosis in B-lineage lymphoid cells. *Science* 273:1096.
21. Vassilev, A., Z. Ozer, C. Navara, S. Mahajan, and F. M. Uckun. 1999. Bruton's tyrosine kinase as an inhibitor of the Fas/CD95 death-inducing signaling complex. *J. Biol. Chem.* 274:1646.
22. Uckun, F. M., W. E. Evans, C. J. Forsyth, K. G. Waddick, L. T. Ahlgren, L. M. Chelstrom, A. Burkhardt, J. Bolen, and D. E. Myers. 1995. Biotherapy of B-cell precursor leukemia by targeting genistein to CD19-associated tyrosine kinases. *Science* 267:886.
23. Ozawa, K., Z. Szallasi, M. G. Kazanietz, P. M. Blumberg, H. Mischak, J. F. Mushinski, and M. A. Beaven. 1993. Ca(2+)-dependent and Ca(2+)-independent isozymes of protein kinase C mediate exocytosis in antigen-stimulated rat basophilic RBL-2H3 cells. Reconstitution of secretory responses with Ca2+ and purified isozymes in washed permeabilized cells. *J. Biol. Chem.* 268:1749.
24. Malaviya, R. and S. N. Abraham. 1995. Interaction of bacteria with mast cells. *Methods Enzymol.* 253:27.
25. Zhu, D. M., R. K. Narla, W. H. Fang, N. C. Chia, and F. M. Uckun. 1998. Calphostin C triggers calcium-dependent apoptosis in human acute lymphoblastic leukemia cells. *Clin. Cancer Res.* 4:2967.
26. Konger, R. L., R. Malaviya, and A. P. Pentland. 1998. Growth regulation of primary human keratinocytes by prostaglandin E receptor EP2 and EP3 subtypes. *Biochim et Biophys Acta.* 1401:221.
27. Smith, P. K., R. I. Krohn, G. T. Hermanson, A. K. Mallia, F. H. Gatner, M. D. Provenzano, E. K. Fujimoto, N. M. Goeke, B. J. Olson, and D. C. Klenk. 1985. Measurement of protein using bicinchoninic acid. *Anal. Biochem.* 150:76.

28. Oettgen, H. C., T. R. Martin, A. Wynshaw-Boris, C. Deng, J. M. Drazen, and P. Leder. 1994. Active anaphylaxis in IgE-deficient mice. *Nature* 370:367.
29. Kligman, L. H., F. J. Akin, and A. M. Kligman, 1982. Prevention of ultraviolet damage to the dermis of hairless mice by sunscreens. *J. Invest. Dermatol.* 78:181.
30. Cronstein, B. N., D. Naime, and G. Firestein. 1995. The antiinflammatory effects of an adenosine kinase inhibitor are mediated by adenosine. *Arthritis & Rhumatism.* 38:1040.
31. Perretti, M., J. G. Harris, and R. J. Flower. 1994. A role for endogenous histamine in interleukin-8-induced neutrophil infiltration into mouse air-pouch: investigation of the modulatory action of systemic and local dexamethasone. *Br. J. Pharmacol.* 112:801.
32. Thastrup, O., P. J. Cullen, B. K. Drobak, M. R. Hanley, and A. P. Dawson. 1990. Thapsigargin, a tumor promoter, discharges, intracellular Ca2+-ATPase. *Proc. Natl. Acad. Sci. USA.* 87:2466.
33. Sagi-Eisenberg, R. 1993. Signal-Transmission Pathways in Mast Cell Exocytosis. *Immunopharmacology of Mast Cells and Basophils.* 71.
34. Woodward, D. F., P. Raval, M. A. Pipkin, and D. A. Owen. 1981. Re-evaluation of the effect of non-steroidal anti-inflammatory agents on u.v.-induced cutaneous inflammation. *Agents Actions.* 11:711.
35. Snyder, D. S., and W. H. Eaglstein. 1974. Topical indomethacin and sunburn *Br. J. Dermatol.* 90:91.
36. Dawson, J., A. D. Sedgwick, J. C. W. Edwards, and P. A Lees. 1991. Comparative study of the cellular exudative and histological responses to carrageenan, dextran in zymosan in the mouse. *Int. J. Tissue. Reac.* 13:171.
37. Hruza, L. L. and A. P. Pentland, 1993. Mechanisms of UV-induced inflammation. *J. Invest. Dermatol.* 100:35S.

We claim:

1. A method treating an inflammation reaction in a subject in need thereof, comprising administering to the subject 2,4,6-trihydroxy-α-p-methoxyphenylacetophenone, or a pharmaceutically acceptable derivative thereof, in an amount sufficient for inhibiting an inflammatory reaction in the subject.

2. The method of claim 1, wherein said treating is prophylactic, remedial, or both.

3. The method of claim 1, wherein 2,4,6-trihydroxy-α-p-methoxyphenylacetophenone, or a pharmaceutically acceptable derivative thereof, is administered to a subject to prevent an inflammation reaction.

4. The method of claim 1, wherein the inflammation reaction is an acute inflammatory reaction.

5. The method of claim 1, wherein the inflammation reaction is an allergic inflammatory reaction.

6. The method of claim 1, wherein the inflammation results from a condition selected from the group consisting of asthma, arthritis, psoriasis, skin sunburn, inflammatory pelvic disease, inflammatory bowel disease, urethritis, uvitis, senusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitis and cholangititis.

7. The method of claim 1, wherein 2,4,6-trihydroxy-α-p-methoxyphenylacetophenone, or a pharmaceutically acceptable derivative thereof, is administered topically.

8. The method of claim 1, wherein 2,4,6-trihydroxy-α-p-methoxyphenylacetophenone, or a pharmaceutically acceptable derivative thereof, is administered systemically.

9. The method of claim 1, wherein 2,4,6-trihydroxy-α-p-methoxyphenylacetophenone, or a pharmaceutically acceptable derivative thereof, is administered orally.

10. The method of claim 1, wherein 2,4,6-trihydroxy-α-p-methoxyphenylacetophenone, or a pharmaceutically acceptable derivative thereof, is administered by injection.

11. The method of claim 10, wherein 2,4,6-trihydroxy-α-p-methoxyphenylacetophenone, or a pharmaceutically acceptable derivative thereof, is administered subcutaneously, intravenously, or intramuscularly.

12. The method of claim 1, wherein 2,4,6-trihydroxy-α-p-methoxyphenylacetophenone, or a pharmaceutically acceptable derivative thereof, is administered transdermally.

13. The method of claim 1, wherein 2,4,6-trihydroxy-α-p-methoxyphenylacetophenone, or a pharmaceutically acceptable derivative thereof, is administered via inhalation.

14. The method of claim 1, wherein 2,4,6-trihydroxy-α-p-methoxyphenylacetophenone, or a pharmaceutically acceptable derivative thereof, is administered vaginally, rectally, or by intracavitary administration.

15. The method of claim 1, wherein 2,4,6-trihydroxy-α-p-methoxyphenylacetophenone, or a pharmaceutically acceptable derivative thereof is administered intraperitoneally.

16. The method of claim 1, wherein 2,4,6-trihydroxy-α-p-methoxyphenylacetophenone, or a pharmaceutically acceptable derivative thereof, is administered intradermally.

17. The method of claim 1, wherein 2,4,6-trihydroxy-α-p-methoxyphenylacetophenone, or a pharmaceutically acceptable derivative thereof, is administered nasally.

18. The method of claim 1, wherein said pharmaceutically acceptable derivative is a salt form.

19. The method of claim 1, wherein said pharmaceutically acceptable derivative is an ester.

20. A method for treating skin sunburn comprising administering to the subject 2,4,6-trihydroxy-α-p-methoxyphenylacetophenone, or a pharmaceutically acceptable derivative thereof, in an amount sufficient for inhibiting an inflammatory reaction in the subject.

21. The method of claim 1, wherein said administering is prior to, during, or after sunburn exposure.

22. A method for treating anaplylaxis comprising administering to the subject 2,4,6-trihydroxy-α-p-methoxyphenylacetophenone, or a pharmaceutically acceptable derivative thereof, in an amount sufficient for inhibiting an inflammatory reaction in the subject.

23. The method of claim 1, wherein said administering is prior to, during, or after onset of an anaphylactic reaction.

* * * * *